United States Patent [19]
Griffith et al.

[11] Patent Number: 5,390,661
[45] Date of Patent: Feb. 21, 1995

[54] INTRODUCER FOR ESOPHAGEAL PROBES

[75] Inventors: Jim Griffith, Phoenix, Ariz.; Cheryl Ried, Pasadena, Calif.

[73] Assignee: W. L. Gore & Associates, Inc., Newark, Del.

[21] Appl. No.: 12,714

[22] Filed: Feb. 3, 1993

[51] Int. Cl.⁶ .............................................. A61B 1/00
[52] U.S. Cl. ....................................... 128/4; 606/108
[58] Field of Search ................... 128/200.26, 207.14, 128/207.15, 207.17, 8, 3, 4, 912, DIG. 26, 6; 606/108

[56] References Cited

U.S. PATENT DOCUMENTS

| | | | |
|---|---|---|---|
| 3,754,554 | 8/1973 | Felbarg | 128/200.26 |
| 3,880,168 | 4/1975 | Berman | 128/207.15 |
| 3,913,565 | 10/1975 | Kawahara | 128/8 X |
| 3,913,568 | 10/1975 | Carpenter . | |
| 3,948,251 | 4/1976 | Hosono | 128/8 X |
| 4,195,624 | 1/1980 | Douglas | 128/8 |
| 4,244,362 | 1/1981 | Anderson | 128/200.26 |
| 4,275,724 | 6/1981 | Behrstock | 128/207.14 |
| 4,449,532 | 5/1984 | Storz | 128/4 X |
| 4,846,153 | 7/1989 | Berci | 128/6 |
| 5,020,534 | 6/1991 | Pell et al. | 128/DIG. 26 X |
| 5,127,393 | 7/1992 | McFarlin et al. . | |
| 5,174,284 | 12/1992 | Jackson . | |

FOREIGN PATENT DOCUMENTS

| | | |
|---|---|---|
| 3326061 | 2/1984 | Germany . |
| 8401512 | 4/1984 | WIPO . |
| 9001350 | 2/1990 | WIPO . |
| 9114391 | 10/1991 | WIPO . |

Primary Examiner—Richard J. Apley
Assistant Examiner—Beverly A. Meindl
Attorney, Agent, or Firm—Gary A. Samuels

[57] ABSTRACT

An introducer is provided which directs a probe, such as TE ultrasound probe, into the esophagus. The introducer of the present invention consists of a pilot member and a coaxially fitting sheath. The pilot member may be an endoscope-like element and the sheath is an elongate flexible member. The outside diameter of the pilot member insertion tube is roughly the same as that of the TE probe while the outside diameter of the sheath is sized for passage into the esophagus. When assembled coaxially, the pilot member and sheath fit slidingly together.

9 Claims, 8 Drawing Sheets

INTRODUCER FOR ESOPHAGEAL PROBES

BACKGROUND OF THE INVENTION

Various probes are inserted into the esophagus for the purposes of medical diagnosis and/or therapy. Diagnostic probes include those for transesophageal echocardiography (TEE). Transesophageal (TE) ultrasound probes consist of an elongate flexible shaft with a transducer on the distal end and a "control handle" on the proximal end. The handle contains controls for defecting the distal tip so that desired views of the heart are obtained.

TE ultrasound probes are preferred over transthoracic probes in certain cases where better quality images are obtained by TEE. Generally speaking, TEE images are superior to transthoracic images for two reasons. First, a TE probe is positioned closer to the heart so that acoustic attenuation is reduced and higher frequency sound waves may be employed. Second, because of probe positioning the sound waves from a TE probe are not hampered by ribs and lungs.

TEE applications include: detection of aortic dissections, locating clots in the left atrium, monitoring ventricular wall motion for myocardial ischemia during coronary bypass surgery, and detecting residual mitral regurgitation during mitral valve repair. Predicting obstructive coronary artery disease by visualizing aortic plaque is recently reported and a particularly exciting application.

Intubating the esophagus with current methods requires considerable experience and is sometimes difficult. Intubation is accomplished by anesthetizing the pharynx, positioning the probe in the back of the throat, asking the patient to swallow, and passing the probe into the esophagus.

There are several disadvantages to the current method of intubating the esophagus. First, the intubation can easily take 10 or 15 minutes. For example, the patient may have trouble swallowing the large diameter (approximately ½ inch diameter [1.27 cm]) TE probe. Also, the physician may have difficulty obtaining the best probe position because only tactile clues are available for probe guidance. Second, the present method occasionally produces tracheal intubation rather than the desired esophageal intubation. Third, certain patients cannot be intubated with a TE probe because of anatomic geometry. Fourth, certain anatomical details such as a pharyngeal pouch serve as contraindications for TEE. Fifth, the physician's fingers are subject to biting and risk of infection during the intubation procedure.

It is an objective of this invention to provide a device(s) which reduces the time required to place a TE probe into a patient's esophagus. Another objective of the invention is to provide a device(s) which ensures that the examiner intubates the correct lumen. Another objective is to provide a device(s) which minimizes intubation problems resulting from unusual anatomy. It is also an objective to provide a device which allows TEE in patients that would be contraindicated for the standard TEE procedure. A further objective is to provide a device which reduces the physician's risk of infection from bites obtained while placing a TE probe in the esophagus. An additional objective of the invention is to provide methods for placing a TE probe into the esophagus.

These and other objectives are obtained by the preferred embodiments described herein.

SUMMARY OF THE INVENTION

An introducer is provided which directs a probe, such as a TE ultrasound probe, into the esophagus. The introducer of the present invention consists of a pilot member and a coaxially fitting sheath. The pilot member may be an endoscope-like element and the sheath is an elongate flexible member. The outside diameter of the pilot member insertion tube is roughly the same as that of the TE probe while the outside diameter of the sheath is sized for passage into the esophagus. When assembled coaxially, the pilot member and sheath fit slidingly together.

Optical components such as fibers and lenses within the pilot member gather an optical image of anatomic structures distal of the introducer and present that image to an examining physician. Tip control components within the pilot member allow the examiner to deflect the distal tip in at least one plane. Torsional stiffness allows the physician to rotate the pilot member and hence realize additional control over the tip position.

In a first embodiment a device somewhat similar to a commonly used medical endoscope with diameter sized to slidingly fit into the sheath can be used as the pilot member.

In a second embodiment the pilot member consists of a small diameter endoscope-like member (say 3 mm insertion tube diameter) and an adapter which is an elongate flexible element. At the distal end the adapter fits slidingly over the small endoscope. At the distal end the outside diameter (O.D.) of the adapter is only slightly larger than that of the endoscope. Proximally, the adapter O.D. becomes larger with a gradual tapered shape until the adapter O.D. becomes a sliding fit to the sheath I.D. The tapered section is preferably about 5 to 15 cm long. In this second embodiment, a single endoscope-like member can be used with various diameter adapters and sheaths to introduce various diameter ultrasound probes into the esophagus.

Most preferably, in the second embodiment the distal tip of the adapter is soft, flexible, and fits closely to the endoscope. This minimizes any chance of trauma to the patient.

In a third embodiment the endoscope-like member and adapter from the second embodiment are essentially joined together as one piece. Thus, in the third embodiment the pilot member contains optics, tip deflection, and taper for easier insertion into the esophagus.

It is understood that the terms "endoscope" or "endoscope-like member" are used herein to denote an elongate flexible device with a handle. The device contains mechanisms for optical imaging and tip position control. These functions are usually supplied in conjunction with other features in commercially available medical endoscopes. Available endoscopes may be used as the pilot member in certain embodiments of the present invention. This does not imply that all of the qualities or features commonly found in endoscopes are required in the pilot member. It is only required that the pilot member enable a viewer at the proximal end to see what is beyond the distal end and to enable that viewer to manipulate the position of the distal tip.

The introducer sheath is flexible but crush resistant so that the lumen remains open when curved and placed inside the esophagus. The distal tip is soft and fits closely around the pilot member to make the device atraumatic.

In the TEE procedure the mouth is usually held open with a bite-block which the TE probe passes through for mechanical protection. In use, the invented introducer passes through this bite-block. Most preferably, the proximal end of the sheath has a mechanical feature which prevents the sheath from passing completely through the bite-block and down the esophagus.

In some applications, the sheath contains at least one radiopaque marker for X-ray viewing. Thus if the sheath were somehow passed into the esophagus or stomach, it could be located on X-ray views and appropriate measures taken.

In certain preferred embodiments the proximal portion of sheath contains an integrally formed bite-block. In some applications, the proximal portion of sheath fastens to a bite-block for positional tethering.

Sheath and pilot member lengths are selected so that they extend from within the upper portion of the esophagus to outside of the patient's front teeth. This makes the sheath on the order of 20 cm long; the pilot member is made longer than the sheath. Lengths can be tailored to fit the patient; for example, elements for pediatric application can be shorter than elements for application in adults.

In some preferred embodiments the sheath and/or pilot member contain mechanical stops, detentes or latches that restrict sheath motion on the pilot member.

The present invention also is directed to methods of placing a medical probe within the esophagus by using apparatus substantially made in accordance with the above-described invention. The patient is prepared in accordance with standard TEE methods. Preparation may include: fasting, light sedation, positioning, and anesthetizing the pharynx. An examiner places the sheath coaxially over the pilot member so that the distal tip of the pilot member extends beyond the sheath. The introducer is positioned at the back of the throat where the examiner uses the optical image and the control mechanisms within the pilot member to align the distal end of the pilot member with the esophagus. When the patient swallows, the esophageal sphincter relaxes and the introducer is advanced into the esophagus. The introducer is positioned sufficiently distally so that the sheath engages the esophagus. The examiner leaves the sheath engaging the esophagus and withdraws the pilot member. Finally, the probe, for example a TE ultrasound probe, may be simply passed through the sheath and positioned ready for ultrasonic imaging.

The examiner may cause the sheath to go with the pilot member when intubating the esophagus by applying finger pressure to the sheath which puts the sheath and pilot member into frictional contact. Frictional forces prevent the sheath from sliding on the pilot member. Releasing the finger pressure enables easy withdrawal of the pilot member. Alternately, the examiner may obviate the need for finger pressure by using an introducer embodiment containing stops or latches which restrict sheath motion on the pilot member during intubation.

A bite-block may be used in the disclosed methods for placing the TE probe within the esophagus. In the usual TE probe placement method the bite-block fits coaxially around the TE probe and then between the patient's front teeth. In an analogous manner, the bite-block may be fit around the introducer and between the patient's front teeth.

DETAILED DESCRIPTION OF THE INVENTION

In general, the apparatus of the present invention includes a pilot member and a sheath for introducing a diagnostic or therapeutic probe into the esophagus. For example, a diagnostic transesophageal ultrasound probe can be introduced. The pilot member is an elongate flexible member with a handle on the proximal end; the flexible member contains optical elements for illuminating internal anatomic structures, elements for forming an image of those structures, and elements for transmitting that image outside the body and to an examining physician. The pilot member handle contains controls which deflect the distal tip of the flexible member in at least one plane. In addition, the distal tip may be rotated by rotating the handle because of the torsional stiffness in the flexible member. The imaging, deflecting, and rotating features allow an examiner to place the pilot member tip near or away from selected anatomic structures.

The sheath is an elongate flexible element with a lumen which allows the pilot member or the TE probe to pass within it to be introduced into the esophagus. A crush resistant lumen remains essentially open so that the pilot member or TE probe slides through freely while the sheath engages the esophagus.

Figure 1:
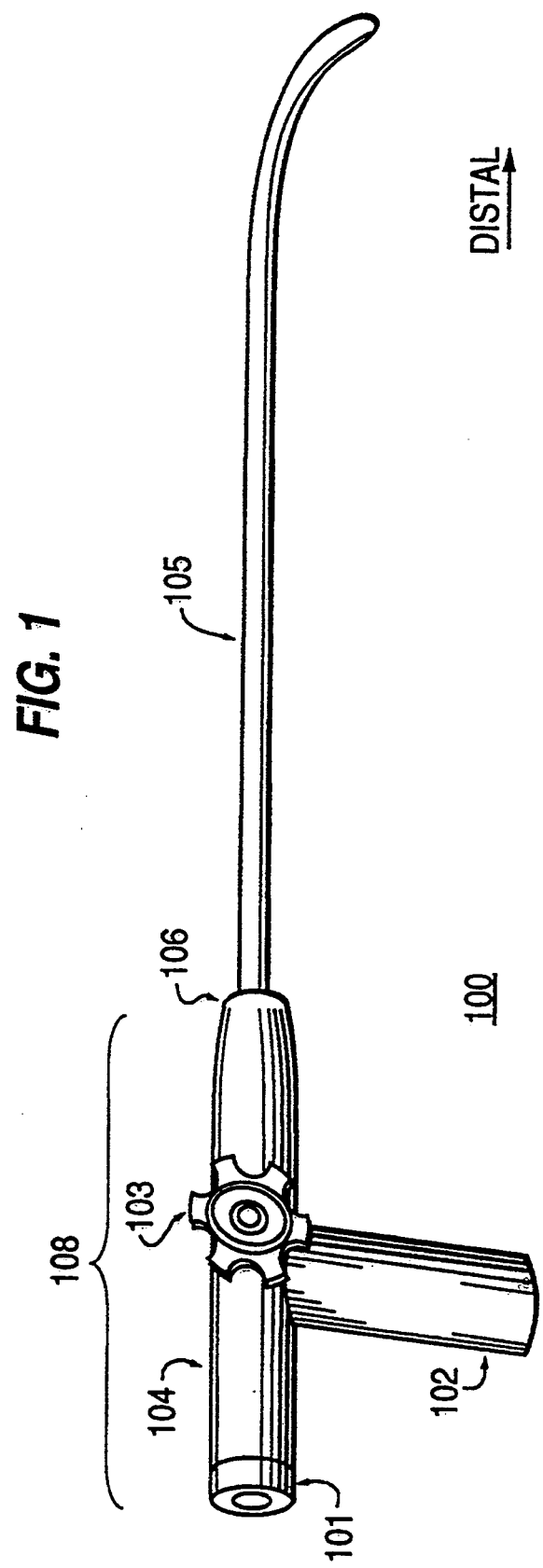
FIG. 1 shows an embodiment of a pilot member made in accordance with the present invention.

A first preferred embodiment of the pilot member 100 appears in FIG. 1. At the proximal end a handle 108 is comprised of an eyepiece 101, a casing 104, a control actuator 103, and a light source inside holder 102. An elongate flexible insertion tube 105 connects with the handle at junction 106. The insertion tube contains elements (not shown) which provide an optical image of that anatomy which is distal of the tube end 107. This image is transmitted to eyepiece 101 where it is available for viewing. The light source inside holder 102 can be a battery powered source providing light for said imaging. Alternately, 102 can represent a connector which allows attachment of a remote light or power source. Control actuator 103 connects with the distal tube of insertion tube 105 via lines contained within tube 105; this enable an operator to deflect the tube tip at 107 to-and-fro in at least one plane. Torsional stiffness provided by tube 105 allows the tip to be rotated by rotating the proximal handle. The diameter of insertion tube 105 closely matches that of the TE or other probe which is to be introduced into the esophagus; the tube 105 will usually have a length of at least about 20 cm to allow it to reach from outside the patient's mouth into the esophagus.

Figure 2:
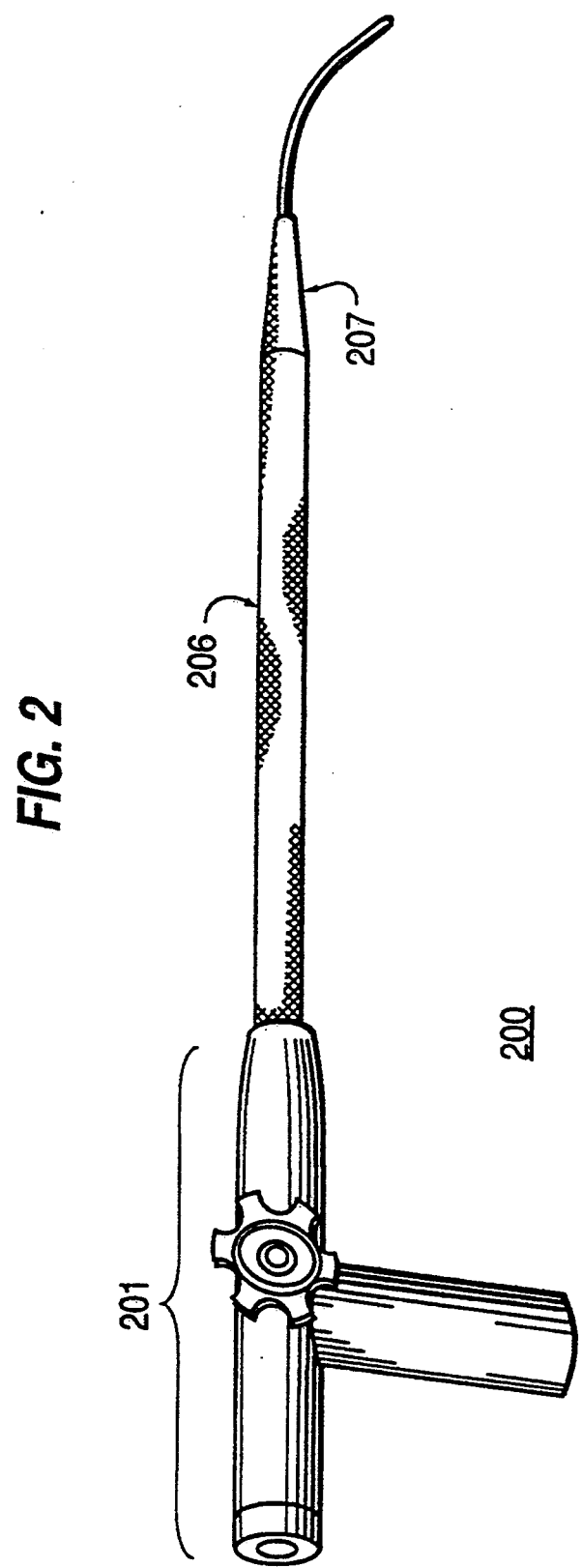
FIG. 2 is a second embodiment of a pilot member made in accordance with the present invention.

A second preferred pilot member embodiment 200 is illustrated in FIG. 2. The proximal handle 201 is unchanged from the description for the first preferred embodiment. But, the insertion tube 206 is considerably changed from the first embodiment. Total length of tube 206 is at least about 20 cm with the exterior diameter of the proximal portion of that length being close to that of the TE or other probe which is to be introduced into the esophagus. Ultrasound probes are often about 15 mm in diameter. A several cm long distal tip portion of tube 206 is smaller in diameter, for example about 3 mm. It is easier to pass a 3 mm diameter tip into the esophagus than to pass a 14 mm diameter tip into the esophagus. A several cm long tapered area 207 makes a smooth transition between the tip diameter and the more proximal diameter. This transition allows an examiner to easily advance the pilot member into the esophagus after the tip engages the esophageal sphincter.

Figure 3:
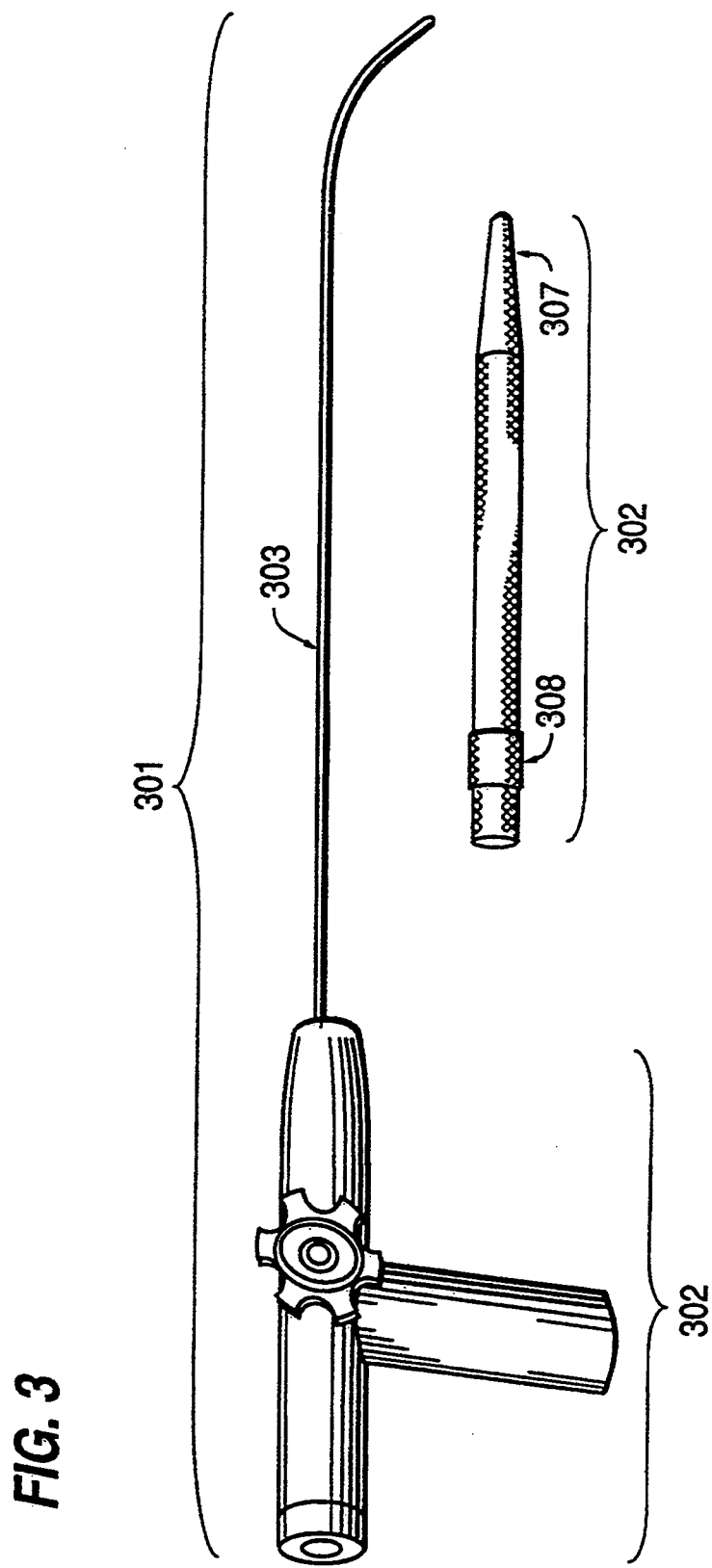
FIG. 3 presents a pilot member implementation consisting of two pieces which fit coaxially together.

A third preferred pilot member embodiment appears in FIG. 3. In this embodiment the pilot member is composed of a director component 301 and an adapter 350. The director 301 has a proximal handle 302 analogous to that in embodiment one. The director has an elongate flexible element 303 extending distally from the handle. The director component 301 houses optical elements which gather images and route them through the eyepiece to an examiner; the director also houses control lines which enable the distal tip to deflect to-and-fro in at least one plane. Torsional stiffness allows the operator to rotate the distal tip by rotating the handle. The director extends into the esophagus from outside the patient's mouth; hence it is at least about 20 cm long. Flexible element 303 has a small diameter, for example 3 mm, at the distal tip and proximally for at least about 20 cm. Flexible elongate adapter 350 is shorter that flexible element 303 but sufficiently long to extend from the esophagus to outside the patient's mouth. Adapter 350 fits coaxially over director 301. A tapered section 307 fits slidingly over the director; the tapered section diameter increases proximally to essentially the diameter of the TE or other probe which is to be introduced later into the esophagus. Adapters with diameters matched to various TE or other probes may be used with a single director 301. Most preferably, a mechanical grip 308 is placed near the proximal end of 350 to minimize slipping in the examiner's hand. Most preferable, the tapered tip 307 is soft, smooth, and flexible to minimize trauma to the patient.

Figure 4:
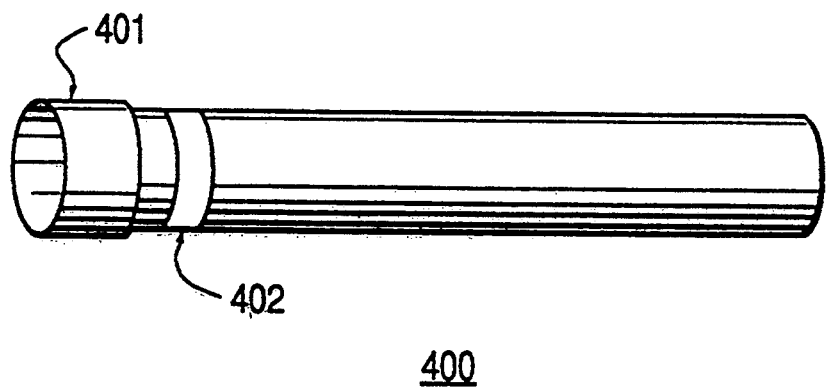
FIG. 4 shows a sheath made in accordance with the present invention.

FIG. 4 depicts the sheath component of the invention in one embodiment. Sheath 400 is an elongate flexible member at least about 30 cm long. The inside diameter of sheath 400 passes, with sliding fit, the TE or other probe that is to be introduced into the esophagus. Most preferably, sheath 400 is a crush resistant tubular structure which remains open in the esophagus to reduce friction on probes introduced through the sheath. A proximal structure or region of enlarged diameter 401 serves as a grip for moving the sheath and as a stop preventing the sheath from sliding too far down the esophagus. It is understood that this region may also be formed into a bite block. Radiopaque X-ray marker 402 allows location of the sheath in X-ray views in the unlikely event that a sheath were swallowed. Most preferably, the distal tip of sheath 400 is soft, flexible, and close fitting about the introduced probe to minimize trauma to the patient. Sheath 400 functions with the pilot members of FIGS. 1-3.

Figure 5:
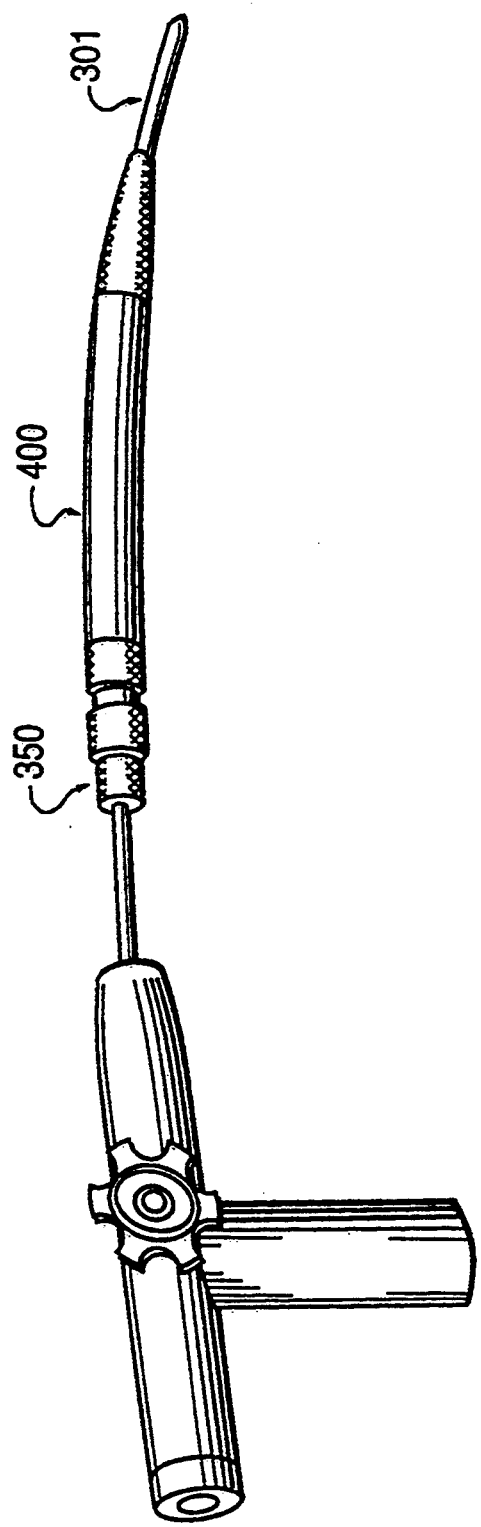
FIG. 5 depicts a pilot member embodiment assembled coaxially with a sheath and ready for insertion into the esophagus.
Figure 6:
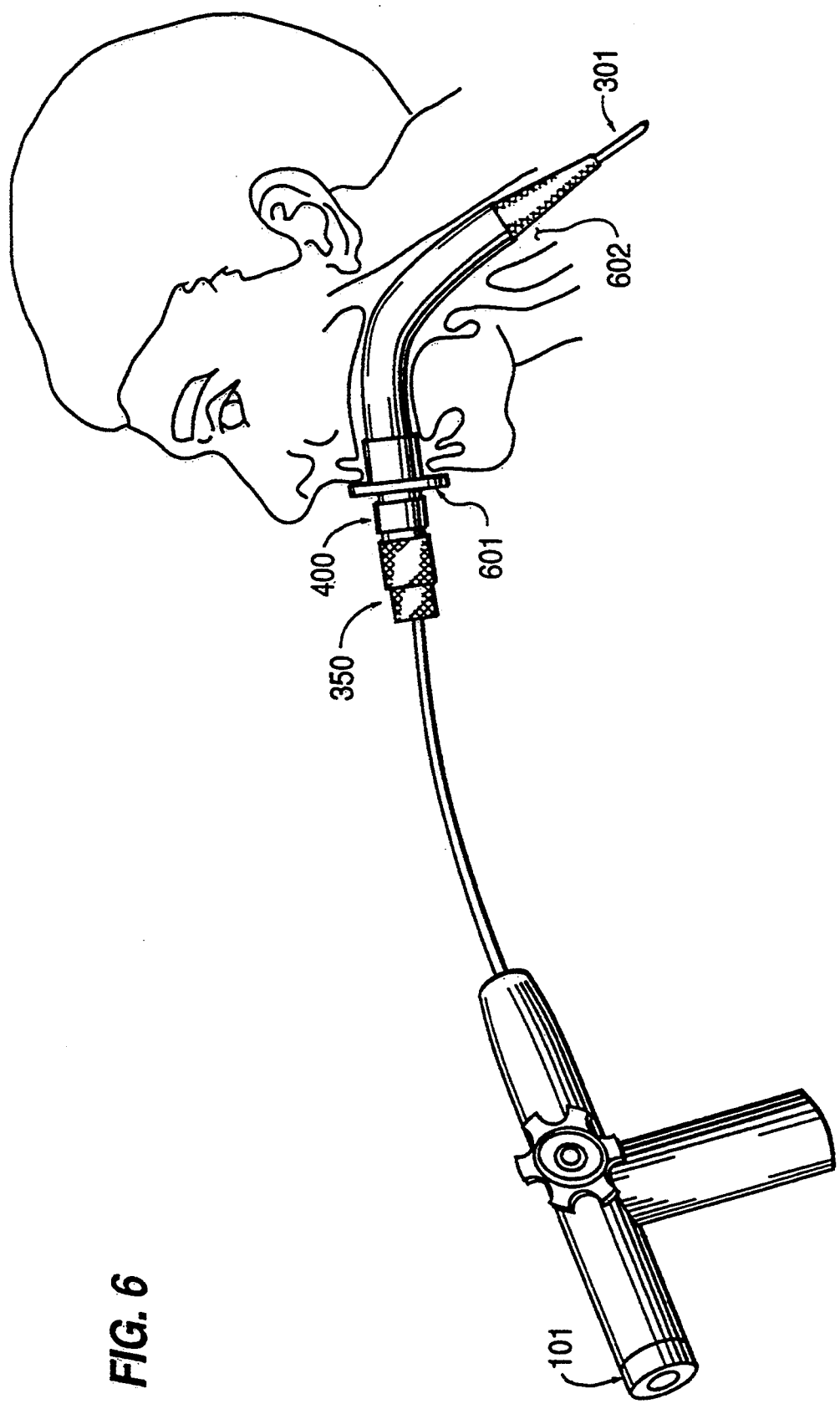
FIG. 6 shows a pilot member and sheath passing into a patient's esophagus.
Figure 7:
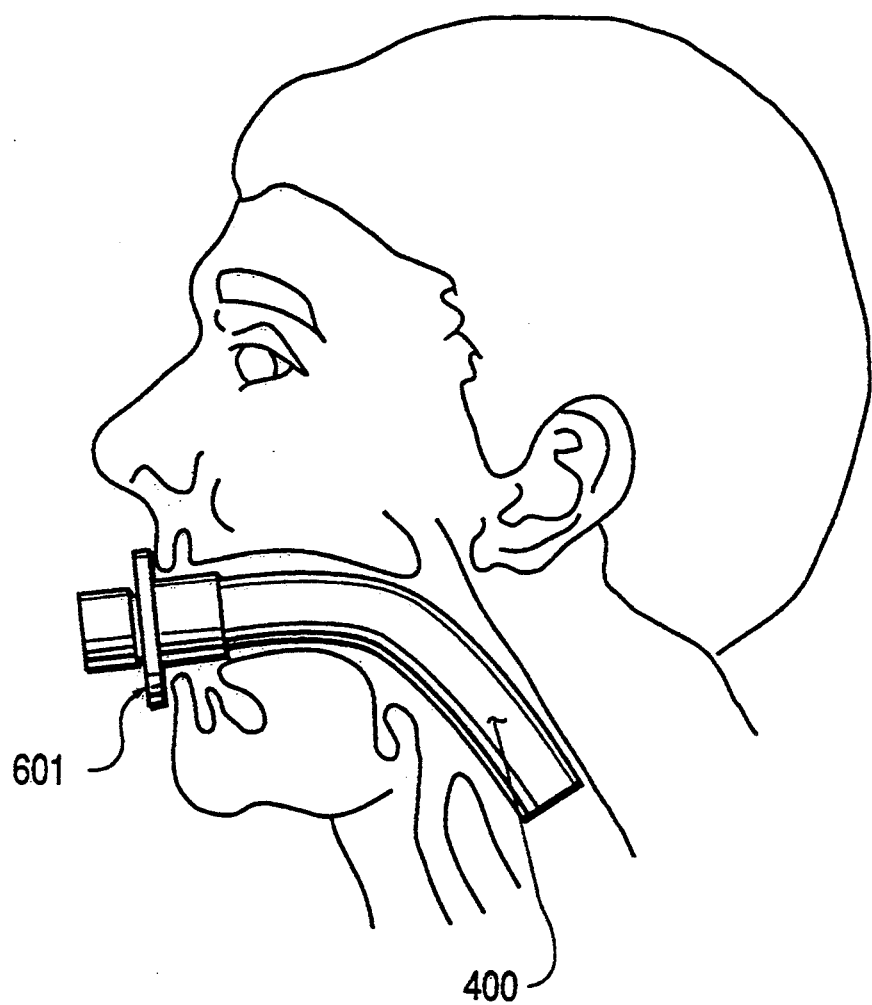
FIG. 7 shows a sheath engaged in the esophagus in preparation for passing an ultrasound probe.
Figure 8:
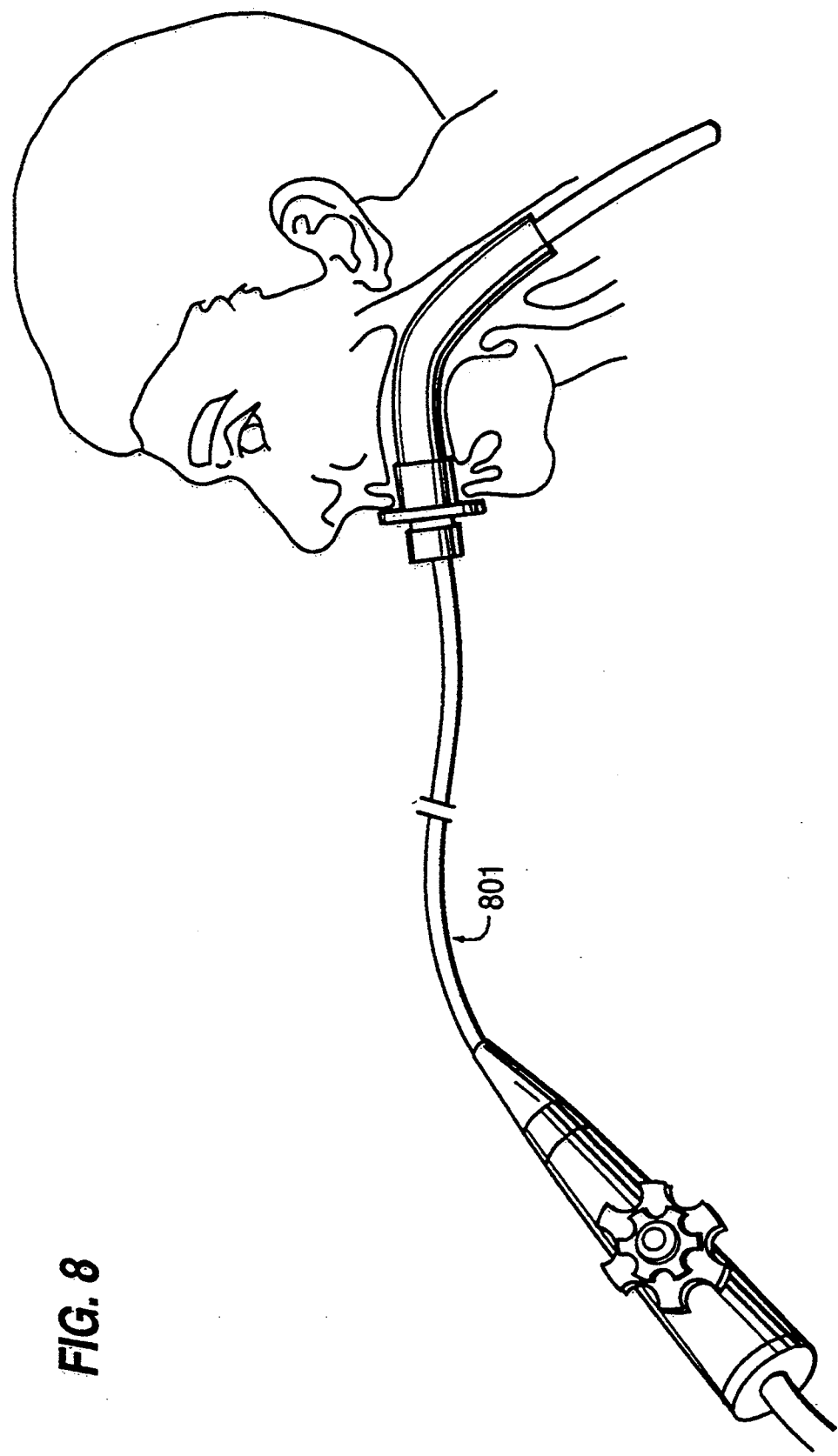
FIG. 8 depicts an ultrasound probe passing through the invented sheath and into the esophagus for cardiac imaging.

The present invention also provides improved methods of introducing a diagnostic or therapeutic probe into the esophagus. For example, the introducer of the invention can be used to place a TE ultrasound probe into the esophagus for cardiac imaging. The patient is prepared and positioned for a TE examination. A sheath and pilot member are assembled coaxially as demonstrated in FIG. 5 where the sheath 400 is placed coaxially over pilot member 301. Obviously, sheath 400 could alternately fit coaxially over pilot members 100 or 200 without materially affecting the example. FIG. 6 shows the introducer passing through a bite block 601 and into a patient's esophagus 602. A physician accomplishes this intubation while viewing anatomic structures through the eye piece 101, positioning the distal tip of the introducer by using the capability for deflection and rotation, and moving the introducer through the esophageal sphincter when the patient swallows. The physician removes the pilot member by pulling it out leaving the sheath placed through the bite-block and engaging the esophagus as shown in FIG. 7. An ultrasound probe 801 is placed ready for cardiac imaging by advancing it through the sheath as indicated in FIG. 8.

Use of the present invention has been described in the context of introducing an ultrasound probe for cardiac imaging. Those of ordinary skill, however, will understand that the introducer could be used to deliver other devices, allowing other signals or substances to be placed into the esophagus for diagnosis or therapy. It is to be understood that the invention can also be used to sequentially introduce various devices into the esophagus by leaving the sheath in place, withdrawing probes or devices, and inserting other probes or devices through the sheath.

We claim;

1. An introducer for passing medical devices or probes into a patient's esophagus, which comprises:
   a pilot member and an elongated flexible crush-resistant tubular sheath of which the length fits coaxially and slidably around said pilot member;
   said sheath constructed to fit into the esophagus of a patient and having a length extending from outside a patient's mouth into the esophagus;
   said pilot member having a proximal handle and a distal insertion tube;
   said insertion tube being an elongate, flexible, tubular element with means for rotating and deflecting the distal tip and optical means for imaging what lies beyond the distal end of said insertion tube;
   said insertion tube handle containing means for controlling the rotation and deflection of said insertion tube.

2. The introducer of claim 1 wherein the distal portion of the insertion tube tapers down to a diameter that is less than the diameter of the more proximal portion said of tube.

3. The introducer of claims 1 or 2 wherein the sheath contains a radiopaque marker.

4. The introducer of claims 1 or 2 wherein the sheath contains a bite-block at the proximal end.

5. An introducer for passing medical devices or probes into a patient's esophagus, which comprises:

a pilot member, and an elongated flexible crush-resistant tubular sheath that fits coaxially and slidably around said pilot member;

said sheath constructed to fit into the esophagus of a patient and having a length extending from outside a patient's mouth into the esophagus;

said pilot member consisting of separable director and coaxially fitting elongate adapter element;

said director having a proximal handle and a small diameter distal elongate flexible element which fits inside the adapter;

said director having provision for positioning the distal tip and optical provision for imaging what lies distally;

the adapter being a flexible elongated tubular member with an outside diameter over most of the length that slidably fits into said sheath; and over about a several cm distal length the outside diameter tapers down to be only slightly greater than that of the flexible element of the director which slidably fits through the adapter.

6. The introducer of claim 5 wherein the sheath contains a radiopaque marker.

7. The introducer of claim 5 wherein the sheath contains a bite-block at the proximal end.

8. A method for introducing a medical instrument or device into the esophagus of a patient comprising the steps of:
   a. providing an introducer consisting of an elongate flexible sheath and a pilot member, in which the pilot consists of a proximal handle and a distal insertion tube which have facility for tip deflection and rotation so that the member can be moved in proximal/distal directions and the distal tip can be positioned in three dimensional space; said pilot member capable of providing optical images on anatomic structures appearing distally; the sheath being crush resistant and fitting coaxially and slidably over the length of the insertion tube; the inside diameter of the sheath being sized to accept the medical instrument which is to be introduced into the esophagus;
   b. placing the sheath coaxially over the insertion tube;
   c. using the position control and optical imaging capability to advance the introducer into the patient's esophagus;
   d. withdrawing the pilot member while leaving the sheath engaged with the esophagus;
   e. advancing the medical instrument or device through the sheath and into the esophagus.

9. A method as in claim 8 comprising the further steps of leaving the sheath in place and changing the medical instrument by sequentially withdrawing and inserting different medical probes and devices.

* * * * *